(12) United States Patent
Roberts

(10) Patent No.: US 9,632,070 B2
(45) Date of Patent: Apr. 25, 2017

(54) APPARATUS FOR CALCULATING FEED VALUE OF ALFALFA HAY USING INFORMATION AVAILABLE AT TIME OF BALING

(71) Applicant: Jeffrey S. Roberts, Hudson, WI (US)

(72) Inventor: Jeffrey S. Roberts, Hudson, WI (US)

( * ) Notice: Subject to any disclaimer, the term of this patent is extended or adjusted under 35 U.S.C. 154(b) by 626 days.

(21) Appl. No.: 13/573,461

(22) Filed: Sep. 17, 2012

(65) Prior Publication Data

US 2014/0081587 A1 Mar. 20, 2014

(51) Int. Cl.
*G01N 33/02* (2006.01)

(52) U.S. Cl.
CPC .................................. *G01N 33/02* (2013.01)

(58) Field of Classification Search
CPC ........................... G01N 33/02; G01N 33/0098
See application file for complete search history.

(56) References Cited

U.S. PATENT DOCUMENTS

| | | | | | |
|---|---|---|---|---|---|
| 4,561,995 | A | * | 12/1985 | Fenn | 252/194 |
| 4,742,880 | A | * | 5/1988 | Schrag | A01F 15/0875 100/99 |
| 4,743,454 | A | * | 5/1988 | Tomes | 426/61 |
| 4,885,531 | A | * | 12/1989 | Stowell | 324/695 |
| 5,226,356 | A | * | 7/1993 | Schrag | B30B 9/3025 100/41 |
| 5,253,570 | A | * | 10/1993 | Goeckner | A01F 15/0825 100/191 |
| 2003/0159421 | A1 | * | 8/2003 | Trelstad | A01F 15/0841 56/341 |
| 2004/0093648 | A1 | * | 5/2004 | Johnson et al. | 800/295 |
| 2005/0210699 | A1 | * | 9/2005 | Philippe et al. | 34/191 |
| 2006/0283166 | A1 | * | 12/2006 | Schlesser | 56/341 |
| 2012/0186465 | A1 | * | 7/2012 | Dresher | A01F 15/101 100/35 |
| 2014/0216280 | A1 | * | 8/2014 | Missotten et al. | 100/35 |

OTHER PUBLICATIONS

Muck et al., Conserved Forage (Silage and Hay): Progress and Priorities, International Grassland Congress. vol. 19, Sao Pedo: SBZ, 2001.*
Rimbey et al., Adjusting Forage Value for Moisture Content, Proceedings, Idaho Alfalfa and Forage Conference Feb. 24-25, 2004.*
Jeranyama et al., Understanding Relative Feed Value (RFV) and Relative Forage Quality (RFQ), 2004.*

* cited by examiner

*Primary Examiner* — John Breene
*Assistant Examiner* — Yaritza H Perez Bermudez
(74) *Attorney, Agent, or Firm* — Skinner and Associates; Joel Skinner

(57) ABSTRACT

A method where the weight of the bale is measured by a scale on the baler, the moisture of the bale is measured by sensors on the baler and this information is sent to a processor. Based on compaction properties of the leaf verses the stem of the alfalfa, the processor calculates a feeding value for the hay including protein, energy and relative feed value on the dry density of the bale. Additional inputs such as the compaction setting of the baler and information about the hay being harvested can also be input into the processor for making adjustment to the feeding value calculation.

8 Claims, 2 Drawing Sheets

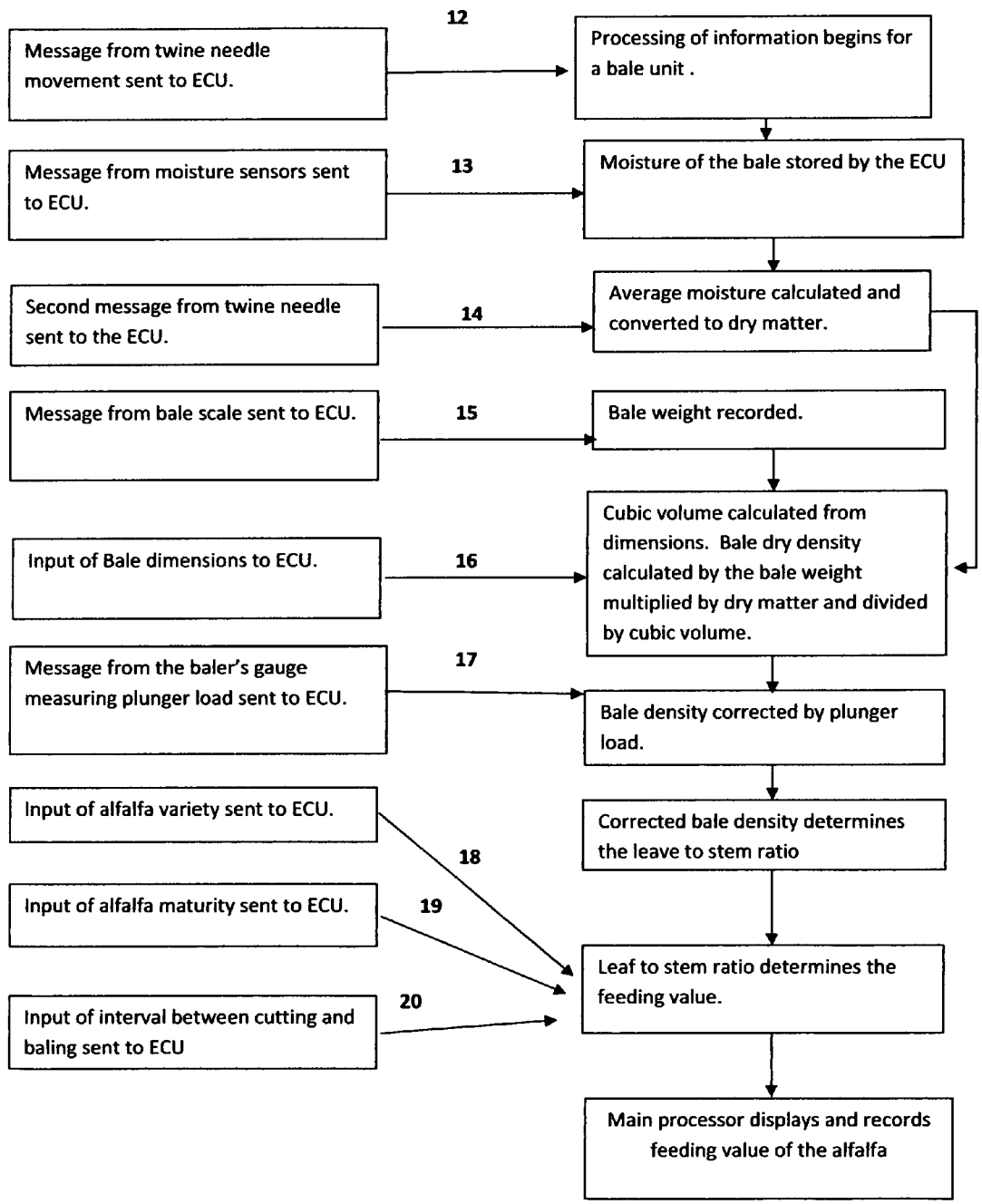

APPARATUS FOR CALCULATING FEED VALUE OF ALFALFA HAY USING INFORMATION AVAILABLE AT TIME OF BALING

CROSS REFERENCE TO RELATED APPLICATIONS

A System and method for identifying bales of hay, U.S. Pat. No. 7,415,924 B2.
A System and Method for Identifying Bales of Hay, U.S. Pat. No. 7,621,111 B2.

THE NAMES OF PARTIES ON A JOINT RESEARCH AGREEMENT

Not Applicable.

STATEMENT REGARDING FEDERALLY SPONSORED RESEARCH FOR DEVELOPMENT

Not Applicable.

BACKGROUND

Alfalfa hay is a primary source of feed for dairy and beef feeding operations. While growing, the alfalfa plant is approximately fifty percent leaves and fifty percent stems. Ninety percent of the feeding value, including protein and relative feed value is in the leaf portion of the plant. The feeding value of alfalfa will vary depending on how it is harvested and the resulting ratio of leaves to stems in the harvested alfalfa crop as the leaves will separate from the stems as it is mechanically handled. The common practice of feeders of alfalfa is to pull samples of the harvested alfalfa and send them into a lab to determine the feeding value, so that the ration fed to dairy and beef livestock can be adjusted with other supplements to feed the correct amount of nutrients to produce milk or meat.

One of the main methods for harvesting alfalfa is to use a hay baler, harvesting the alfalfa under sixteen percent moisture content so that the alfalfa does not spoil due to a higher moisture. As the alfalfa dries, it becomes difficult to keep the leaves on the plant as it is baled and the leaves are separated from the stem with the mechanical action of the baler. When baling at sixteen percent moisture, the finished bale will be approximately forty percent leaves and sixty percent stems as the mechanical action of the baler separates some of the leaves. When the hay dries from sixteen down to thirteen percent moisture, additional leaves are separated during baling so the finished bale will be thirty percent leaves and sixty percent stems. This change in the leave to stem ratio leads to a significant reduction in the feeding quality. Multiple tests for the feeding quality are required to identify the different levels of nutrient value between bales due to variation of the moisture at harvest.

Recently, balers have been commonly equipped with a scale device to weigh the bales being made. The leaf portion of the alfalfa plant which is flat will compress to a higher density than the stem portion of the plant which is round. Tests run on alfalfa samples at 16% moisture in a compression chamber with six hundred pounds per square inch of pressure applied, which is similar to the compression applied during baling, illustrate how the properties of compression are influenced by the ratio of leaves and stems as follows:

| % LEAVES | % STEMS | BALE WEIGHT | BALE VOLUME (3 FT × 3 FT × 8 FT BALE) | DENSITY OF SAMPLES (POUNDS PER CUBIC FOOT) |
|---|---|---|---|---|
| 100% | 0% | 1440 POUNDS | 72 CU FT | 20 pounds |
| 80% | 20% | 1296 POUNDS | 72 CU FT | 18 pounds |
| 60% | 40% | 1152 POUNDS | 72 CU FT | 16 pounds |
| 50% | 50% | 1080 POUNDS | 72 CU FT | 15 pounds |
| 40% | 60% | 1008 POUNDS | 72 CU FT | 14 pounds |
| 30% | 70% | 936 POUNDS | 72 CU FT | 13 pounds |
| 20% | 80% | 864 POUNDS | 72 CU FT | 12 pounds |
| 10% | 90% | 720 POUNDS | 72 CU FT | 10 pounds |
| 0% | 100% | 576 POUNDS | | |

Ninety percent of the feeding value of alfalfa is in the leaf portion of the plant. As the leaf to stem ratio changes, the feeding value of the alfalfa also changes as measured by two important values of the feeding quality, protein and relative feed value (RFV). Feeding quality tests run on alfalfa samples at 16% moisture with various leaf to stem ratios show the following values:

| | | TESTED FEED QUALITY | |
|---|---|---|---|
| % LEAVES | % STEMS | PROTEIN | RELATIVE FEED VALUE |
| 100% | 0% | 28% | 240 |
| 80% | 20% | 26% | 220 |
| 60% | 40% | 24% | 200 |
| 50% | 50% | 23% | 190 |
| 40% | 60% | 22% | 180 |
| 30% | 70% | 20% | 160 |
| 20% | 80% | 16% | 120 |
| 10% | 90% | 14% | 100 |
| 0% | 100% | 12% | 80 |

Recently, balers have been equipped with moisture sensors. As moisture is added to a bale of hay, the weight of the bale changes, due to the weight of the water within the bale.

A test of a bale fourteen inches by sixteen inches by thirty-six inches (4.66 cubic feet) demonstrate the change in weight as water is added to the bale:

| % moisture content | bale weight |
|---|---|
| 10% | 46.6 pounds |
| 12% | 47.5 pounds |
| 14% | 48.5 pounds |
| 16% | 49.6 pounds |
| 18% | 50.7 pounds |
| 20% | 51.8 pounds |
| 22% | 53.0 pounds |

In the method that has been invented, factoring in the moisture of the bale to the weight of the bale, gives an estimate of the leaf to stem ratio and therefore a method for calculating its feeding value.

BRIEF SUMMARY OF THE INVENTION

In the method that has been invented, the weight of the bale is measured by a scale on the baler, the moisture of the bale is measured by sensors on the baler and this information is sent to a processor. Based on compaction properties of the leaf verses the stem of the alfalfa, the processor calculates a feeding value for the hay including protein, energy and relative feed value on the dry density of the bale. Additional inputs such as the compaction setting of the baler and information about the hay being harvested can also be input into the processor for making adjustment to the feeding value calculation.

BRIEF DESCRIPTION OF SEVERAL VIEWS OF THE DRAWINGS

FIG. 2 shows a flow chart of the processing of inputs from the baler to predict feeding quality.

DETAILED DESCRIPTION OF THE INVENTION

Figure 1:
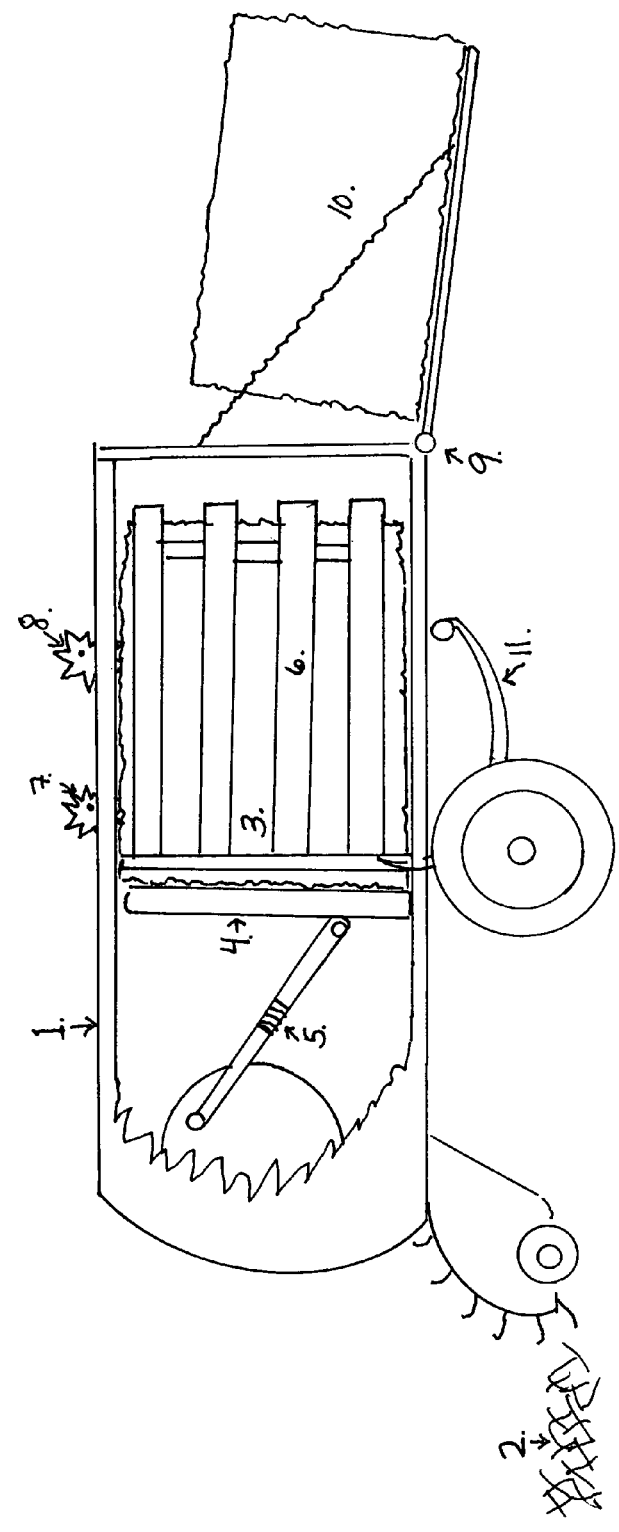
FIG. 1 shows a baler with the weighing system, moisture testing system and compaction system.

A hay baler 1 Picks up alfalfa from a windrow 2 to form a bale 3. The baler's plunger mechanism 4 compacts the bale and a gauge 5 senses the load of compaction from the plunger. The plunger pressure against the hay is regulated by increasing or decreasing the size of the chamber by setting the position of the doors 6 to squeeze the hay into a fixed area. The moisture of the bale is read by conductivity between two metal star wheels land 8 on the formed bale 3. As the bale is delivered out of the baler, it is weighed by a scale device picking up signals from load cells at critical points 9. The bale weight is read on a completely formed bale 10 that is separated from the previous bale 3 as it is delivered from the baler to get an isolated reading from the load cells 9. A needle 11 routes the twine which holds the individual bales together and its movement is sensed in this method to identify each bale as a contiguous unit.

To calculate the feeding value of the bale of alfalfa, information is received from the weight and moisture sensors on the baler and processed by an electronic control unit (ECU). In the memory of the ECU, a table of feeding quality is stored for the protein, relative feed value and other related quality measurements based on the dry density of alfalfa hay. The steps in the processing begin with the needle 11 sending a message to the ECU 12 when it moves signaling that the twine has been routed up through the hay defining the start of the bale. Readings for percent moisture from the moisture sensors 7 and 8 are sent to the ECU 13 and stored in the ECU until the next message from the twine needle 11 is received 14 signaling the end of the bale. After receiving that message the ECU calculates average moisture for the bale formed between the two movements of the needle. The ECU converts the moisture reading to a dry matter value by subtracting the moisture percent from one hundred percent.

When the bale moves to a position 10, the bale scale 9 will see an increase in weight readings as the portion of the bale resting in the scale increases. When this weight reaches a maximum, the bale scale reading sent to the ECU 15 is recorded as the weight of the bale.

A means for inputting the dimension of the bale is provided to the ECU 16. The cubic volume of the bale is calculated from these dimensions by the ECU. The ECU uses the bale weight multiplied by the dry matter percent and divides that by the cubic volume to calculate a dry density of the bale. The ECU then compares the corrected dry density of the bale to a look up table in memory and displays and records the feed value for the bale.

The load reading for the baler's plunger load sensor 5 can be sent to the ECU 17 to correct the density calculated. The ECU then compares the corrected dry density to a look-up table stored in the memory of the ECU, and records and displays a feed value for the bale.

Further corrections can be input into the ECU. Some plant varieties of alfalfa are higher in feed value than others. Correction factors can be input into the ECU 18 for known varieties of alfalfa and a selection of those varieties sent to the ECU which corrects the displayed and recorded feed value.

Maturity of the alfalfa at harvest can affect feeding value. Correction factors can be input into the ECU 19 for a selection of maturities of the alfalfa. A selection of maturities can be sent to the ECU and the feeding values can be corrected for the displayed and recorded feed values.

The interval between cutting and baling can also affect the feeding value of the alfalfa. Correction factors for the hours of time between cutting and baling can be input into the ECU 20. A selection of hours between cutting and baling can be sent to the ECU which corrects the displayed and recorded feed value.

What is claimed:

1. A baler apparatus for baling alfalfa hay and for determining the nutritional feed value of alfalfa hay in a bale baled by the baler apparatus, based on the ratio of leaves to stems, comprising a baler including a hay pickup, a plunger mechanism, a bale forming area, and a bale output, a means to measure, disposed on the baler, the weight and the moisture of a bale of alfalfa of a predetermined size, a processor, disposed on the baler, to calculate a dry density of the bale based on weight, moisture and size of the bale, and to compare the dry density of the bale to a table of feed values with respect to the ratio of leaves to stems, based on dry density stored in a memory of the processor, and to record and display the iced value, wherein the plunger is communicatively connected to the bale forming area and further comprising a load sensor communicatively connected to the plunger, and where force of compaction is read from the load sensor and used to further correct the feed value recorded and displayed.

2. The baler apparatus of claim 1 were a variety of alfalfa is entered into the processor and used to further correct the feed value recorded and displayed.

3. The baler apparatus of claim 1 where a maturity of the alfalfa is entered into the processor and used to further correct the feed value recorded and displayed.

4. The baler apparatus of claim 1 where time interval between cutting of the alfalfa and baling of the alfalfa is entered into the processor and used to further correct the feed value recorded and displayed.

5. The baler apparatus of claim 1, wherein the means to measure the weight and the moisture of a bale of alfalfa includes at least two conductivity star wheels.

6. The baler apparatus of claim 1, further comprising a twine router disposed on the baler, and wherein the twine router is communicatively connected to the processor to determine the start and end of a bale forming cycle.

7. A baler apparatus for baling alfalfa hay and for determining the nutritional feed value of alfalfa hay in a bale baled by the baler apparatus, based on the ratio of leaves to stems, comprising a baler including a hay pickup, a plunger mechanism, a bale forming area, and a bale output, a means to measure, disposed on the baler, the weight and the moisture of a bale of alfalfa of a predetermined size, a processor, disposed on the baler, to calculate a dry density of the bale based on weight, moisture and size of the bale, and to compare the dry density of the bale to a table of feed values with respect to the ratio of leaves to stems, used on dry density stored in a memory of the processor, and to record and display the feed value, wherein a time interval between cutting of the alfalfa and baling of the alfalfa is entered into the processor and used to further correct the feed value recorded and displayed.

8. A baler apparatus for baling alfalfa hay and for determining the nutritional feed value of alfalfa hay in a bale baled by the baler apparatus, based on the ratio of leaves to stems, comprising, a baler including a hay pickup, a plunger mechanism, a bale forming area, and a bale output, a means to measure, disposed on the baler, the weight and the moisture of a bale of alfalfa of a predetermined size, a processor, disposed on the baler, to calculate a dry density of the bale based on weight, moisture and size of the bale, and to compare the dry density of the bale to a table of feed values with respect to the ratio of leaves to stems, based on dry density stored in a memory of the processor, and to record and display the feed value, wherein the means to measure the weight and the moisture of a bale of alfalfa includes at least two conductivity star wheels.

* * * * *